(12) United States Patent
Wang et al.

(10) Patent No.: US 11,500,045 B1
(45) Date of Patent: Nov. 15, 2022

(54) SHIELDING OF A PORTABLE MRI SYSTEM

(71) Applicants: Zepp, Inc., Cupertino, CA (US); Anhui Huami Health Technology Co., Ltd., Anhui FTZ (CN)

(72) Inventors: Jinghua Wang, Cupertino, CA (US); Kongqiao Wang, Anhui FTZ (CN); Liyun Lu, Anhui FTZ (CN)

(73) Assignees: Zepp, Inc., Cupertino, CA (US); Anhui Huami Health Technology Co., Ltd., Anhui FTZ (CN)

(*) Notice: Subject to any disclaimer, the term of this patent is extended or adjusted under 35 U.S.C. 154(b) by 0 days.

(21) Appl. No.: 17/373,406

(22) Filed: Jul. 12, 2021

(51) Int. Cl.
*G01R 33/28* (2006.01)
*A61B 5/055* (2006.01)
*G01R 33/421* (2006.01)

(52) U.S. Cl.
CPC ............ *G01R 33/288* (2013.01); *A61B 5/055* (2013.01); *G01R 33/421* (2013.01); *A61B 2560/0431* (2013.01)

(58) Field of Classification Search
None
See application file for complete search history.

(56) References Cited

U.S. PATENT DOCUMENTS

| | | | |
|---|---|---|---|
| 5,028,872 A * | 7/1991 | Nakabayashi | G01R 33/421 324/318 |
| 5,986,531 A | 11/1999 | Carrozzi | |
| 6,188,015 B1 | 2/2001 | Curran, Sr. et al. | |
| 7,733,089 B2 | 6/2010 | Hobbs et al. | |
| 9,470,769 B2 * | 10/2016 | Bilu | G01R 33/422 |
| 9,535,141 B2 | 1/2017 | Rapoport | |
| 9,562,956 B2 | 2/2017 | Rapoport | |
| 10,012,711 B2 | 7/2018 | Rapoport | |
| 10,078,122 B2 | 9/2018 | Rapoport | |
| 10,134,495 B2 | 11/2018 | Easley | |
| 10,191,127 B2 * | 1/2019 | Strauss | A61B 5/0077 |
| 10,274,561 B2 | 4/2019 | Poole et al. | |
| 10,433,729 B2 | 10/2019 | Overweg et al. | |
| 10,495,704 B2 | 12/2019 | Rapoport | |
| 10,539,637 B2 | 1/2020 | Poole et al. | |

(Continued)

FOREIGN PATENT DOCUMENTS

| | | |
|---|---|---|
| WO | 2005036185 A2 | 4/2005 |
| WO | 2018098267 A1 | 5/2018 |

*Primary Examiner* — Rodney E Fuller
(74) *Attorney, Agent, or Firm* — Young Basile Hanlon & MacFarlane, P.C.

(57) ABSTRACT

A portable system has a magnet, magnet bore and shielding. The magnet bore extends through the magnet, and the magnet bore configured to receive at least some portion of a patient. The shielding forms a shielding area, and the shielding includes one or more layers. The shielding has a material that provides magnetic shielding that reduces or prevents a static magnetic field (SMF); a material that provides electromagnetic shielding and reduces or prevents a time-varying-electromagnetic field (EMF); a removable shielding removable or movable, wherein the patient is able to move into our out of the magnet bore when the removable shielding is in a moved position or a removed position and the removable shielding; and a shielding adapter covering a connection of devices and extending from the exterior of the portable system. All or a portion of the shielding includes a transparent portion.

20 Claims, 3 Drawing Sheets

(56) References Cited

U.S. PATENT DOCUMENTS

| | | |
|---|---|---|
| 10,684,335 B2 | 6/2020 | Poole et al. |
| 10,698,050 B2 | 6/2020 | Poole et al. |
| 10,718,835 B2 | 7/2020 | Poole et al. |
| 10,976,393 B2 | 4/2021 | Rapoport et al. |
| 2003/0088175 A1* | 5/2003 | Branch ................ G01R 33/422 600/410 |
| 2005/0049491 A1* | 3/2005 | Rezzonico ............ A61B 5/055 600/436 |
| 2008/0129068 A1* | 6/2008 | Brummel ................ B60P 3/14 361/818 |
| 2008/0186026 A1* | 8/2008 | Leussler .............. G01R 33/422 324/318 |
| 2017/0146619 A1* | 5/2017 | Strauss ................ H04N 5/2253 |
| 2018/0164389 A1* | 6/2018 | Rapoport ............. G01R 33/422 |
| 2018/0224512 A1* | 8/2018 | Poole .................... G01R 33/383 |
| 2020/0249293 A1* | 8/2020 | Saunders ............... A61B 90/11 |
| 2021/0318400 A1* | 10/2021 | Thakore ............... G01R 33/422 |
| 2022/0022829 A1* | 1/2022 | Oakes .................... A61B 46/40 |

* cited by examiner

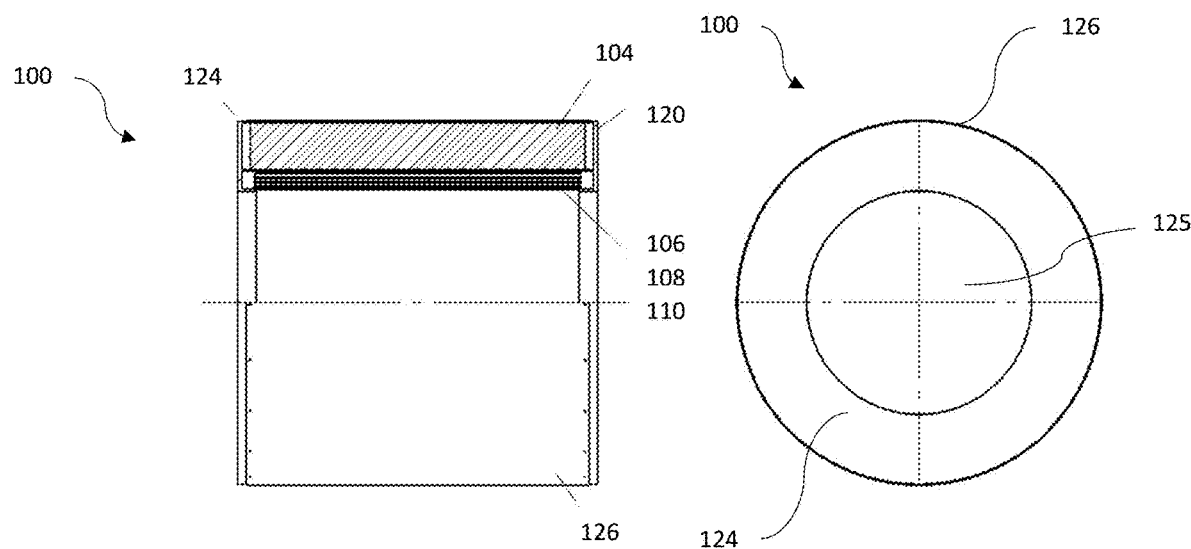
Figure 2A
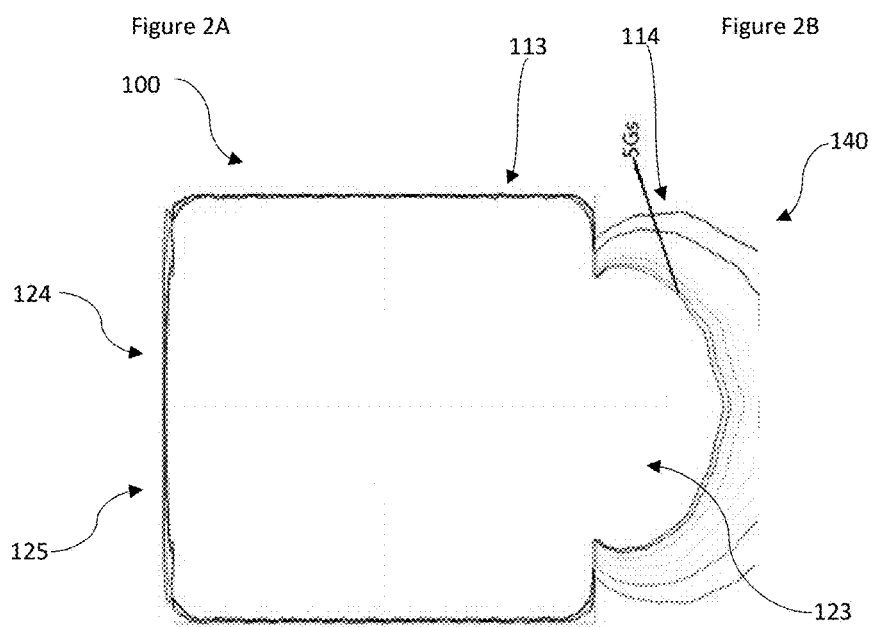
Figure 2B
Figure 3

SHIELDING OF A PORTABLE MRI SYSTEM

FIELD

This disclosure relates generally to a portable magnetic resonance imaging (MRI) system and shielding of a static magnetic field (SMF) and time-varying electromagnetic field (EMF) produced by the MRI system and adjacent electrical devices so that the MRI can be safely and effectively used.

BACKGROUND

Many diseases and abnormal body conditions (such as tumors, strokes, heart problems, spine diseases, etc.) can be detected using magnetic resonance imaging (MRI). MRI creates images that can show differences between healthy and unhealthy tissue. MRIs can be a safer imaging technology than, for example, x-ray or computed tomography (CT) because patients and medical personnel are not subjected to ionizing radiation exposure during the imaging procedure. To obtain an image of a region of interest (ROI), a powerful, constant magnetic field, rapidly changing local magnetic fields, radiofrequency (RF) energy, and dedicated equipment are used.

The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution.

In order to obtain a detectable MR signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

Currently, the trend in clinical MRI has been to increase the field strength of MRI scanners to improve image quality and efficiency (i.e. scan time, signal-to-noise ratio, temporal-spatial. resolution, contrast, etc). However, a rough cost estimate for a clinical MRI scanner is on the order of one million dollars per tesla, which does not include the substantial operation, service, and maintenance costs at high-field MRI systems, such as RF shielding, cryogen quench vents, cooling infrastructure, or specialized electrical feeds. The high cost and substantial space requirements of high-field MRI systems results in limited availability of MRI scanners. As a result, worldwide only one-tenth of the population has access to MRI scanner. Additionally, the higher specific absorption rate (SAR), susceptibility artifacts, an extension of the Ti time, and reduced Ti contrast are disadvantageous at high-field MRI system. Most recently, there is an increasing interest in the MRI community for low-field MRI system. Though the low-field MRI system cannot provide the highest-quality images, it should be able to provide diagnostically useful information. Additionally, low-field MRI system may have the following advantages. First is the reduced financial cost for MRI system and its maintenance. Second is the reduced siting requirements in terms of space/power/cooling. Third is the reduced acoustic noise, SAR and susceptibility artifacts. Finally, low-field portable MRI systems have the potential to make MR imaging possible at sites where it is currently unavailable and enable immediate, "point-of-care" detection and diagnosis of acute, subacute, and chronic intracranial pathology. In this disclosure, we will focus on the low-field portable MRI systems.

SMF and EMF negatively affects MRI operation and MRI image quality. Particularly, portable MRI systems must be available for various complex electromagnetic environments. Portable MRI systems include a strong static magnetic field within and surrounding the magnet. The SMF of 5 Gauss or more is limited within the magnet bore to reduce the potential dangers for patients and medical devices.

Additionally, the electromagnetic interference around the portable MRI scanner, resulted from an external source such as from electric lines, television and radio signals, light, and elevators, strongly impact the quality of acquired MR images. Conventionally, fixed or mobile MRI scanners are shielded using Faraday cage or shielding room to attenuate static or slowing varied magnetic field, and radio-frequency electromagnetic field. The closed cage or house greatly isolate the MRI system operation room and routine space. As for a portable MRI system, the shielding is limited by limited space and a complex and various electromagnetic environment. Attempts have been made to create an MRI that includes construction and/or design which attenuate SMF and EMF to various degrees. The magnetic shielding may attenuate the SMF of a magnet of the portable MRI system to avoid the potential risk of relatively strong SMF to human and electric device safety, particularly when SMF of a portable MRI system is more than 5 Gauss. Additionally, the electromagnetic shielding attenuate the external EMF from surrounding electric devices on image quality during the portable MRI scanner operation.

Some examples of shielding MRI devices may be found in U.S. Pat. Nos. 5,986,531; 6,188,015; 7,733,089; 9,535,141; 9,562,956; 10,433,729; 10,495,704; 10,012,711; 10,078,122; 10,134,495; 10,191,127; 10,539,637; 10,976,393; 10,274,561; 10,684,335; 10,698,050; and 10,718,835; PCT Patent Application Publication Nos. WO2005/036185 and WO2018/098267 all of which are expressly incorporated by reference herein for all purposes.

SUMMARY

The present teachings provide a portable system comprising: a magnet; a magnet bore, and shielding. The magnet bore extending through the magnet, the magnet bore configured to receive at least some portion of a patient. The shielding that forms all or a portion of an exterior the portable system and forms a shielding area, wherein the shielding includes one or more layers. The shielding comprises: a material the provides magnetic shielding, a material that provides electromagnetic shielding, a removable shielding; and a shielding adapter. The material that provides the magnetic shielding that reduces or prevents a static magnet field (SMF) inside of the shield area from extending outside of the shield area. The material that provides the electromagnetic shielding and reduces or prevents a time-varying-electromagnetic field (EMF) from extending outside of the shield area or into the shield area of the portable system. The removable shielding that is removable or movable, wherein the patient is able to move into or out of the magnet bore when the removable shielding is in a moved position or a removed position and the removable shielding is configured to completely close the shield area so that the portable system is operative. The shielding adapter covering a connection of devices and extending from the exterior of the portable system into the magnetic bore of the portable system, wherein the removable shielding reduces or prevents the SMF from extending outside of the shield area; the EMF from entering the magnet bore of the portable system; or both. All or a portion of the removable shielding includes a transparent portion that is transparent.

The present teachings provide a portable system comprising: a magnet; a shield area, an exterior, and shielding. The shield area is configured to receive all or a portion of a patient. The shielding forms the exterior and extends around all or a portion of the portable system. The shielding includes a removable shielding that is removable or movable from an opening of the shield area so that when the removable shielding is in a moved position or a removed position the patient is able to extend into or out of the opening, and the removable shielding reduces or prevents electrical fields from extending into the opening or out of the opening. The shielding includes a foil, a mesh, a net, or a combination thereof of electrically conductive materials that form an electrically conductive metal, an electrically conductive layer, or both that are part of the shielding, the removable shielding, or both so that all or a portion of the shielding, the removable shielding, or both include a transparent portion. The shielding, the removable shielding, or both reduces the SMF extending outside of the portable system to be about 5 Gauss or lower and the external EMF entering into the portable system to be attenuated by 100 dB or more.

The present teachings provide: a portable system comprising: a magnet, a shield area, an exterior, and shielding. The shield area is configured to receive all or a portion of a patient. The shielding comprises: a material, a rear shielding, a front shielding, an exterior shielding, a removable shielding, and a shielding adapter. The material blocks or reduces electrical fields, radiofrequency, or both, and the material includes a mu-metal, low carbon steel, a nickel-iron alloy, copper, iron, aluminum, or a combination thereof. The rear shielding, including the material, extending over a rear of the portable system. The front shielding, including the material, extending over a front of the portable system and including an opening. The exterior shielding, including the material, extending between and connecting the rear shielding to the front shielding. The removable shielding that includes the material and is configured to extend over the opening and all or a portion of a patient within the portable system so that the removable shielding reduces or prevents the electrical fields, the radiofrequency, or both from extending into the opening or out of the opening, wherein all or a portion of the removable shielding is transparent. The shielding adapter that covers a connection of devices that extend from the exterior of the portable system to the shield area of the portable system.

The present teachings provide an apparatus to shield SMF and (EMF) in a portable MRI/MRS system. The shielding when connected together may form a shield area. The present teachings provide techniques for shielding EMF in the portable MRI/MRS system, which improve the shielding of EMF and provide better quality of acquired MRI images with the portable MRI. The present teachings provide a shielding apparatus that shields SMF and EMF in all directions and completely isolate the shield area from of the MRI from interference outside of the portable MRI scanner. The present teachings also provide specially designed removable shielding (e.g., clothing or blankets) that are used to cover the rest of unshielded parts by solid shielding. The solid removable shielding includes at least one part of visible shielding design to ensure the visibility of the device and the patient. The techniques described herein can be applied in a wide range of applications including the portable MRI/MRS, but are not limited to, a mobile MRI/MRS.

The present device shields EMF in a portable MRI/MRS system, the device includes a magnetic shielding component, which can reduce the leakage of the SMF of a magnet to the outside of a magnet bore which accommodates at least a portion of a subject; the magnetic shield component comprising at least one of removable magnetic shielding which can cover parts of the subject under MRI examination and prevent any possible leakage of SMF; the magnetic shield component comprising at least one part of magnetic shielding materials which are transparent for light under MM examination; an electromagnetic shielding component, which can reduce the electromagnetic interference resulted from outside the magnet; the electromagnetic shielding component comprising at least one of removable electromagnetic shielding which can cover parts of the subject under MRI examination and prevent from the external EMF from exterior the portable MM system; the electromagnetic shield component comprising at least one part of electromagnetic transparent materials which are transparent for light under MM examination; and a shielded adapter provides a sterile connection of electric advices between exterior and the magnet bore the shielding apparatus magnet.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 2A is a side view of a portable MRI system including shielding.

FIG. 2B is an end view of the portable MRI system of FIG. 2A.

FIG. 3 is a top view of the portable MRI system illustrating an electrical field exiting the portable MRI system.

DETAILED DESCRIPTION

Figure 1A:
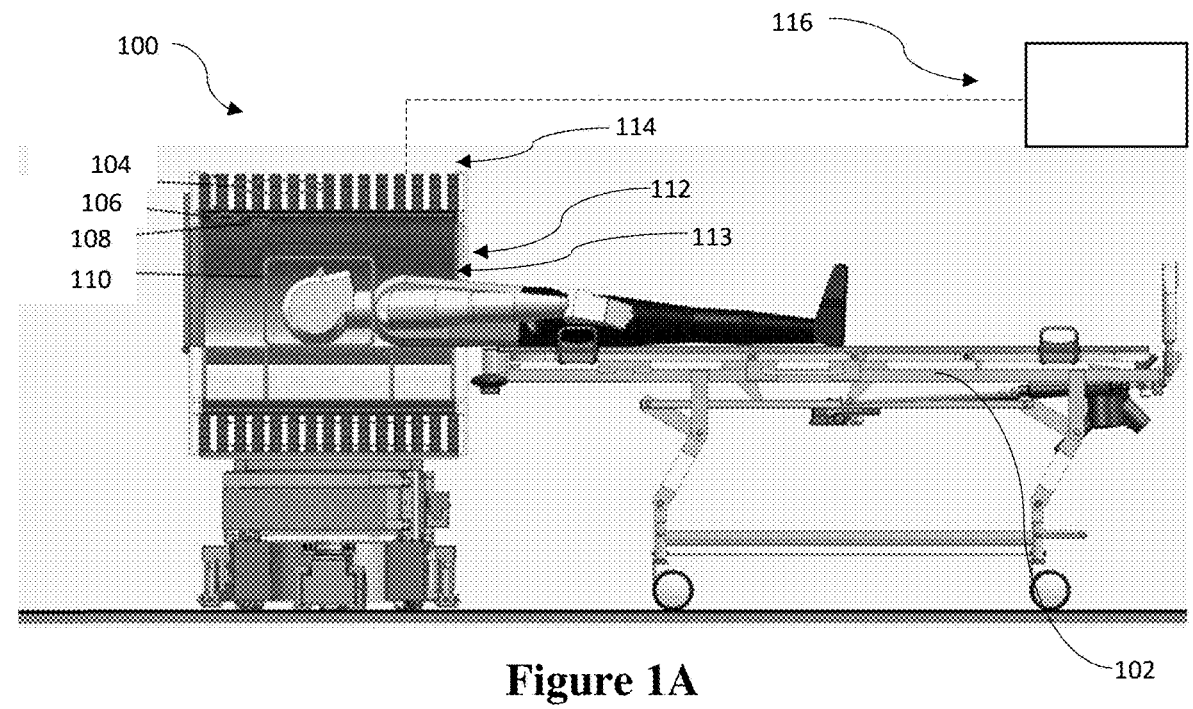
FIG. 1A illustrates an example portable MRI system with shielding removed so that a permanent magnet is exposed.

The present teachings relate to a portable magnetic resonance imaging (MRI) system, a portable magnetic resonance spectroscopy (MRS) system, or both (referred to herein as a portable system or the portable system). The portable system may be self-contained so that the system may be moved from room to room and once plugged in, turned on, or both, the device may function. The portable system may include one or more magnets. The magnets may be a superconducting magnet, a permanent magnet, a resistive magnet, or a combination thereof. The magnets include at least one opening that is configured to receive all or a portion of a patient.

The portable system may include one or more of the magnets discussed herein. The magnets may be generally annularly shaped. The magnets may have a magnet bore. All or a portion of a patient may extend into the magnet bore. The magnet bore may be an interior of the portable system or a portion of a shield area of the portable system. As discussed herein any region outside of the shield area may be considered external of the portable system (e.g., exterior). However, the shield area may be expanded such that the magnet bore is only a portion of the shield area. The shield area may be expanded by adding one or more removable shielding. The removable shielding may extend the shield area so that the magnet bore is not the only portion of the shield area of the portable system. Thus, the shield area may extend beyond the magnet bores so that the shield area may reduce or attenuate EMF, SMF, or both.

The portable system may include a shield that contains substantially all or all of the electrical fields generated by the portable system, prevents external electromagnetic fields (EMF) from entering the portable system, or both. The shielding may reduce the electromagnetic interference (e.g., EMF and SMF) by 50 decibels (dB) or more or 100 dB or more so that a maximum electromagnetic interference rating measured around the portable system is attenuated to be 100 dB or less or 50 dB or less. The shielding may restrict or prevent EMF with a frequency of about 100 MHz or less, about 50 MHz or less, about 15 MHz or less, or about 25 MHz or less. The shielding may restrict or prevent EMF from external devices with a frequency of about 1 KHz or more, about 50 KHz or more, about 100 KHz or more, 1 MHz or more, about 10 MHz or more, about 50 MHz or more, or about 100 MHz or more. The shielding may restrict or prevent an amount of EMF with frequencies between about 1 KHz and about 30 MHz or about 1 KHz or about 10 MHz. The shielding may restrict an amount of EMF that passes through the shield entering the magnet bore so that the EMF noise that extends through is attenuated by about 100 dB or more, about 80 dB or more, about 70 dB or more, or about 50 dB or more (±5 dB).

The EMF interference that usually results from electromagnetic radiation, electromagnetic induction, or a combination thereof may be an interference that is derived from any source natural or artificial, for example, earth magnetic field, atmospheric noise, truck, electrical lines, subways, cellular communication equipment, electrical devices, TV and radio stations, elevators, and so on. The EMF interference can distort the magnetic field uniformity, and change the transmitted and received RF signals, therefore resulting in either artifacts or missing information of the images acquired with an MRI system.

The shielding (e.g., EMF shielding) may substantially enclose an exterior of the portable system. The shielding may isolate a portable system from an external EMF. The shielding may cover or envelop all or a portion of a patient, radiofrequency coils, gradient coils, magnets, or a combination thereof. The shielding may be magnetic shielding. The shielding functions to contain electrical fields within the portable system, prevent EMF from entering the portable system, or both. The shielding may be one or more pieces, two or more pieces, three or more pieces, four or more pieces, or five or more pieces. The shielding may include front shielding, rear shielding, exterior shielding, shielding clothing, a shielding blanket, a shielding adapter, removable shielding, or a combination thereof. The shielding when in communication, connected together, or spread out may cover or form a shield area. All or a portion of the shielding may be opaque, transparent, or both. The shielding may connect together to form one contiguous outer wall. The shielding may overlap one another so that no gaps are present being shielding layers. The shielding may be made of or include a material that restricts static magnetic fields (e.g., SMF), a time-varying electromagnetic field (e.g., EMF), or both. The shielding may be made of or include: plastic, mu-metal, low carbon steel, no carbon steel, a steel alloy, plastic, lead, copper, graphene, brass, nickel, silver, steel, tin, conductive polymers, metal grids, random metallic networks, carbon nanotubes, nanowire meshes, ultra-thing-metal films, or a combination thereof.

The shielding (e.g., magnetic shielding) may be high magnetic permeability metal alloys, such as mu-metal, ferromagnetic metals and metal alloy. The shielding may be part of an MRI system and a portable permanent MRI system.

The shielding (e.g., electromagnetic shielding) may be a shield apparatus for reducing the electromagnetic field around shielded regions using conductive materials. The device or an apparatus for electromagnetic shielding can reduce the influence of the external electromagnetic interference environment on MR image quality by reflection, absorption, or by carrying the electromagnetic radiation to ground. The shielding may include metallic casing, impregnation of a conductive polymer, and conductive coating, conductive plastics, and conductive clothing. In some embodiments, adequate grounding can improve electromagnetic shielding. The shielding may include waveguides, RF filters, waveguide filter, capacitators, and electrically conductive materials, that can be used to attenuate the influence of the external electromagnetic environment on the quality of images acquired with the portable MRI system. For example, the conductive metals, such as copper, aluminum can be used to achieve shielding.

The shielding may surround or substantially surround internal components such as the permanent magnet, the gradient coils, the radio transmission transmission coil (e.g., RF TX Coil), the radio transmission reception coil (e.g., RF RX Coil), or a combination thereof. The internal components may produce heat, an EMF, radiation, or a combination thereof of the shielding material may shield the heat, the electrical field, the radiation, or a combination thereof from exiting the shielding. The shielding may retain the heat, the electrical field, the radiation, or a combination thereof in an interior or a shield area of the portable system; prevent exterior heat, electrical fields, radiation, or a combination thereof from interfering with the portable system; or both. The shielding may be or include an insulative material. The shielding may be or include fiberglass, mineral wool, cellulose, a foam, a polyurethane foam, a polystyrene, or a combination thereof. The shielding may include one or more materials, two or more materials, three or more materials, or four or more materials. The materials may block both EMF and SMF. One material may block EMF and one material may block SMF. In another example, one material may provide magnetic shielding and a second material may provide electromagnetic shielding. The materials may be combined together to form a single layer. The materials when combined together may form a shielding layer. The shielding may extend around an opening so that a user or patient may be placed within and removed from the portable system. The shielding may have a transparent portion.

The transparent portion may allow a user to see a doctor or some other medical professional or vice versa. The transparent portion may allow light to enter the portable system. The transparent portion may function as part of the shielding. The transparent portion may be located opposite an opening.

The opening may be free of shielding. The opening may be covered by a removable shielding (e.g., shielding clothing or shielding blanket). The opening may include a shutting assembly that may close the opening (e.g., when the device is not in use or is being moved). The removable shielding may entirely close the opening when the opening is empty, includes all or a portion of a patient, or both. The removable shielding as discussed herein may be a shielding clothing or a shielding blanket. The removable shielding may cover a portion of a patient not located within the portable system. The removable shielding functions to cover all or a portion of the patient, the opening, or both. The removable shielding may be flexible, rigid, semi-flexible, or a combination thereof. The removable shielding may allow some electrical field, SMF, EMF, or a combination thereof to extend outside of the portable system but restrict the electrical field SMF, EMF, or a combination thereof within a confined space. The removable shielding may include one or more layers that prevent or restrict SMF, EMF, or both. The removable shielding may include one or more layers, two or more layers, three or more layers, or even four or more layers. The removable shielding may include a single layer of shielding material. The removable shielding may include one or more layers, two or more layers, three or more layers, or four or more layers of shielding material. For example, one material may provide magnetic shielding and a second material may provide electromagnetic shielding. The removable shielding may function as an extension of the shielding. The removable shielding may include some transparency so that light, a visual, or both can extend to the patient. The removable shielding may open so that a patient may extend into the opening and then close to stop the electrical field.

The removable shielding may include protective layers, shielding layers, thermal layers, transparent layers, or a combination thereof. The shielding layers may be a single layer of material. The shielding layer may be a single layer that blocks both EMF and SMF. The shielding layer may be one or more materials, two or more materials, three or more materials, or even four or more materials. For example, one material of the shielding layers may block SMF and one material of the shielding layer may block EMF. The removable shielding may be a blanket, a tarp, a drape, a skirt, inflatable cushion, or a combination thereof. The removable shielding may have one or more of the layers discussed herein, two or more of the layers, multiple of one layer, or a combination thereof.

FIG. 1 is a side view of a portable system 100 (e.g., an MRI or MRS system). The portable system 100 may be movable and usable with any patient table 102 or bed. The patient table may be raised or lowered to a height of the portably system 100 or the portable system 100 may be raised or lowered to a height of the patient table 102. The portable system 100 includes a permanent magnet 104. The permanent magnet 104 surrounds the patient while the patient is located in a magnet bore 113 of the permanent magnet 104. The permanent magnet 104 may work in conjunction with gradient coils 106.

The gradient coils 106 may assist the permanent magnet 104 in creating an electric field. The electric field (e.g., a strong static magnetic field) may be created in any direction of an x, y, z, coordinate system. The portable system 100 includes a radio transmission transmission coil (RF TX Coil) 108 transmits electric fields which move the magnetic fields created by the permanent. A radio transmission reception coil (RF RX Coil) 110 receives and measures the electric field moved by the RF TX Coil 108. The electric fields measured by the RF TX coils 108 and RF RX Coils 110 pass through a patient located within an interior 112 of the portable system 100, which as shown in FIG. 1A is the magnet bore 113 within the permanent magnet 104. The RF TX coil 108, the RF RX Coils 110, or both may operate within a radio frequency of about 200 MHz or less, about 100 MHz or less, about 50 MHz or less, or about 25 MHz or less. The RF TX coil 108, the RF RX Coils 110, or both may operate within a radio frequency of about 1 KHz or more, about 50 KHz or more, about 100 KHz or more, about 1 MHz or more, or about 10 MHz or more. Preferably, the RF TX coil 108, the RF RX Coils 110, or both may operate within a radio frequency of about 1 MHz to about 10 MHz.

The magnet bore 113 of the portable system 100 may be sufficiently large to fit all or a portion of a human. The magnet bore 113 may fit a torso of any individual. The magnet bore 113 may have a length that is about 1 m or more, about 1.25 m or more, about 1.5 m or more, or about 1.75 m or more. The magnet bore 113 may have a length that is about 2.5 m or less, about 2.25 m or less, or about 2 m or less. The magnet bore 113 may have cross-sectional length (e.g., diameter) of about 0.5 m or more, about 0.75 m or more, or about 1 m or more. The magnet bore 113 may have a cross-sectional length of about 2 m or less, about 1.5 m or less, or about 1.25 m or less. The cross-section of the portable system 100 may be symmetrical, asymmetrical, circular, oval, geometric, nongeometric, or a combination thereof. The magnet bore 113 of the portable system may be spaced apart from the exterior 114 by walls of the portable system 100. The magnet bore 113 may be an interior of the portable system. The magnet bore 113 may receive all or a portion of a patient. The magnet bore 113 may include a shutter that is openable or closeable. The shutter may be a plate that is moved over the removable shielding 122. A computing device 116 is connected to the portable system 100 to control the portable system and provide feedback to a user.

Figure 1B:
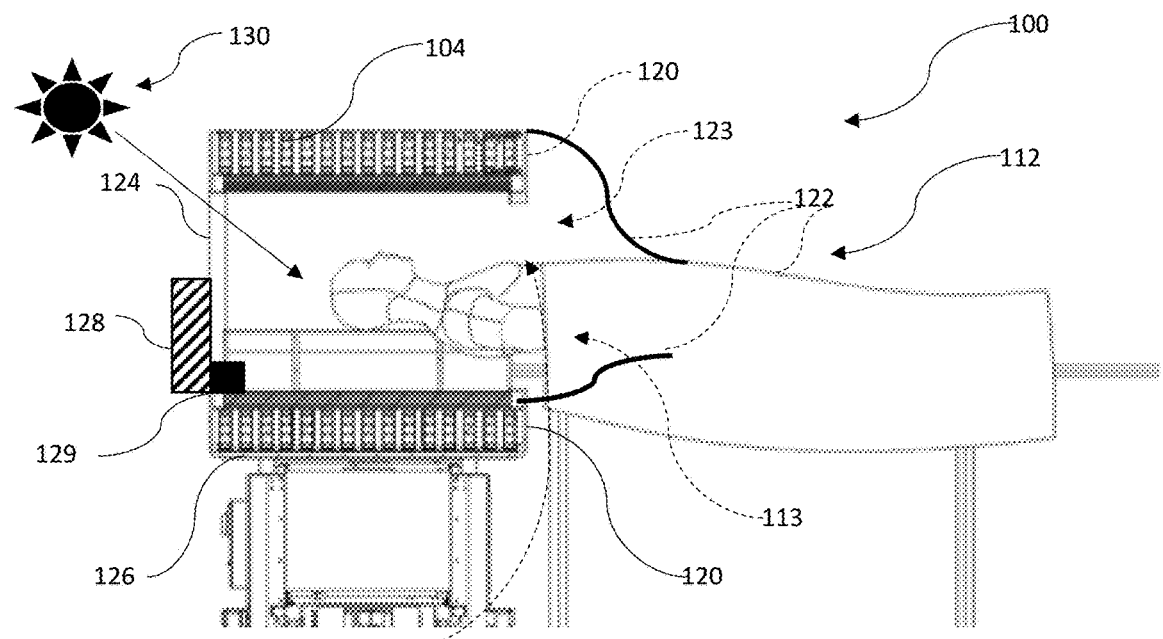
FIG. 1B illustrates a portable MRI system of FIG. 1A including shielding.

FIG. 1B illustrates the portable system 100 of FIG. 1A with shielding applied around the permanent magnet 104. The portable system 100 includes a front shielding 120 covering a front side of the portable system 100. The front shielding 120 may have a shape that is circular, toroid, doughnut, is free of a center, has an external circumference and an internal circumference, or a combination thereof. The front shielding 120 may cap a front of the permanent magnet 104.

A removable shielding 122 is connected to the front shielding 120 and extends over an open end 123 (e.g., an opening) of the magnet bore 113 to extend the shield area 112 of the portable system 100 so that any electrical field that exits the magnet bore 113 through the open end 123 is contained within the shield area 112 by the removable shielding 122. The removable shielding 122 may be movable over the magnet bore 113, extend the shield area 112 beyond the magnet bore 113, or both. As illustrated, the shield area 112 is the region covered by shielding including the removable shielding 122. The removable shielding (clothing or blanket) 122 may prevent leakage of any SMF. The removable shielding 122 includes a shielding layer that restricts or stops an EMF from entering the magnet bore 113. The removable shielding 122 may extend from the portable system 100 to a body of the user so that the removable shielding 122 closes the opening. The removable shielding 122 may be opaque. The removable shielding 122 may be partially or fully transparent. The portable system 100 may include one or more, two or more, three or more, four or more, or even five or more removable shielding 122. As shown a first side of the portable system 100 includes three removable shielding 122 to extend the shield area 112. The removable shielding 122 may extend from and cover a first end, a second end, or both of the magnet bore 113. The removable shielding 122 may extend from the front shielding 120 (e.g, a first end) away from a rear shielding 124 (e.g., a second end).

The front shielding 120, the rear shielding 124, or both may include or be a movable shutting assembly that entirely opens or entirely closes an opening 132 in the portable system 100. For example, a portion of the front shielding 120 and the rear shielding 124 may be removable or movable such that there are two openings and all or a portion of a patient may extend all of the way through the portable system 100 (e.g., an arm or a leg may extend through the magnet bore 113). In another example, only the front shielding 120 or the rear shielding 124 may be removable or movable (e.g., a flap that is folded up or moved to the exterior 114 of the portable system 100) such that one end may remain closed.

The rear shielding 124 may cover an entire rear surface of the portable system 100. The rear shielding 124 may be free of any openings. The rear shielding 124 may be solid, a circle, an oval, completely close one end of the portable system, opaque, partially transparent, completely transparent, mirror a shape of the portable system, or a combination thereof. The exterior shielding 126 may include a transparent portion 125. The rear shielding 124 may connect with, overlap, be part of, or a combination thereof an exterior shielding 126.

The exterior shielding 126 functions to connect the front shielding 120 to the rear shielding 124. The exterior shielding 126 may be connected to the rear shielding 124, the front shielding 120, or both. The exterior shielding 126 and the rear shielding 124, the front shielding 120, or both may be a monolithic piece, connectable, form a unitary surface, include an overlap, or both. The exterior shielding 126 may cover a primary surface or an exterior of the portable system 100, the permanent magnet 104, or both. The exterior shielding 126 may cover a cylindrical surface of the portable system 100, the permanent magnet 104, or both. The exterior shielding 126 may mirror a shape of the portable system 100, the permanent magnet 104, or both. The exterior shielding 126 may be one or more pieces, two or more pieces, three or more pieces, or a combination thereof. The exterior shielding 126 may be one monolithic piece. The exterior shielding 126 may be more than one piece that are connected together to form a single piece (e.g., welded, heat staked, melted, bonded, or a combination thereof). The exterior shielding 126 may by cylindrical, half circular, circular, symmetrical, non-symmetrical, geometric, non-geometric, or a combination thereof. The exterior shielding 126 may connect to the rear shielding 124, a shielding adapter 128, or both.

The shielding adapter 128 functions to provide a sterile connection of device or electrical components extending between an exterior an and an interior of the portable device. The shielding adapter 128 may extend around devices such as cords, wires, connections, connectors, power inlets, signal inlets, air conditioning, communication devices, medical equipment, a temperature sensor, blood pressure sensor, electrocardiogram, electroencephalograph, eye tracking sensor, or a combination thereof. The shielding adapter 128 or passage that the devices pass through may include an RF filter that prevents coupling of RF to the wires or cords passed into the magnet bore 113. The shielding adapter 128 may cover holes in the exterior shielding 126 that allow cords to extend therethrough to provide power to the gradient coils 106, RF TX coil 108, RF RX coils 110, or a combination thereof. The shielding adapter 128 may have a depth so that cords, plugs, wires, or a combination thereof may stick outward, be housed within, be entirely located within, or a combination thereof. The shielding adapter 128 may be removable, permanent, removably attached (e.g., hingedly attached), or a combination thereof. The shielding adapter 128 may be sufficiently large to hold one or more wires, cords, and/or cables; two or more wires, cords, and/or cables, three or more wires, cords, and/or cables, or four or more wires, cords, and/or cables. The shielding adapter 128 extends over all or a portion of a bore 129.

The bore 129 functions to allow devices covered by the shielding adapter 128 to extend into or out of the magnet bore 113. For example, cords, wires, signal wires, cooling, or a combination thereof may extend from an exterior to the magnet bore 113 of the portable system 100. The bore 129 may be sufficiently large to receive or permit one or more devices to extend through the bore 129. The bore 129 may provide access to the magnet, the magnet bore 113 of the portable system 100, or both. The bore 129 may be the magnet bore that includes a movable shutting assembly that may close the bore when the portable system 100 is not in use. The bore 129 may be entirely closed when the portable system 100 is not in use or is being transported. The bore 129 may receive a radiofrequency coil.

The shielding adapter 128 may be located proximate, adjacent, or below the transparent portion 125 of the rear shielding 124 so that light from a light source 130 may extend therethrough.

The light source 130 may be any light (e.g., natural light, a light bulb, fluorescent light, an LED, the sun, or a combination thereof). Light from the light source 130 may extend through the transparent portion 125 of the rear shielding 124. The transparent portion 125 of the rear shielding may be 100 percent transparent (e.g., similar to glass or plastic). The transparent portion 125 may have a transparency less than 100 percent. The transparency may be about 10 percent or more, 20 percent or more, 30 percent or more, 40 percent or more, 50 percent or more, 60 percent or more, 70 percent or more, 80 percent or more, or about 90 percent or more. The transparency may be created by holes or some transparency of the material assembled to form the rear shielding 124. The holes may be a mesh or net material. The transparency may be formed from a combination of holes or mesh in an opaque material (e.g., metal) and a clear material such a polymer. The transparency of the material may allow light to pass through but people or objects on another side of the material may be obscured. The transparency may allow light to pass through and the patient and medical staff may be able to see one another. The transparency may allow for visual communication. Despite the transparency the transparent portions 125 of the rear shield may block electrical fields. The transparent portions 125 may be or include plastic, an insulator material, an overmolding material, conductive polymers, metal grids, random metallic networks, carbon nanotubes, graphene, nanowire meshes, ultra-thin metal fins, or a combination thereof. The conductive polymers, metal grids, random metallic networks, carbon nanotubes, graphene, nanowire meshes, ultra-thin metal films, or a combination thereof may be embedded within another material (e.g., a polymer).

FIG. 2A is a side view of the portable system 100 without a patient. The portable system 100 includes shielding surrounding the working components of the portable system 100. The working components of the portable system 100 includes the permanent magnet 104, the gradient coils 106, the RF TX coil 108 and the RF RC coil 110. The working components are covered by shielding that includes the front shielding 120, the rear shielding 124, and the exterior shielding 126. The front shielding 120, the rear shielding 124, and the exterior shielding 126 all connect together to form one singular shielding that is free of gaps for electric field to escape from the portable system 100. All of the working components are located within the shielding so that the shielding prevents electrical fields from entering or exiting the portable system to cause interference.

FIG. 2B illustrates an end view of the portable system 100 of FIG. 2A. As shown the rear shielding 124 is connected to the exterior shielding 126. The rear shielding 124 includes a transparent portion 125 so that light may pass through, visual contact may be made, the medical staff may see the patient, the patient may see the medical staff, or a combination thereof. The transparent portion 125 may be all or a portion of the rear shielding 124. As shown, the transparent portion 125 is a middle of the rear shielding 124 where working components are not present.

FIG. 3 illustrates the portable system 100 and static magnetic fields 140 extending from the magnet bore 113 to the exterior 114 of the portable system 100 through an open end 123. As shown, the static magnetic fields 140 may not have a magnetic density of 5 Gauss or more a predetermined distance from the portable system 100. However, as shown in FIG. 1B the removable shielding 122 prevents any leakage of static magnetic fields 140 and especially electrical fields of greater than 5 Gauss a predetermined distance from the portable system. The shielding 120, 122, 124, 126, 128 of FIGS. 1B and 2A limits the electrical field within the shielding 120, 122, 124, 126, 128 so that the static magnetic field 140 is retained within the magnet bore 113 and is prevented from extending to surrounding regions, devices, or people. The rear shielding 124 includes a transparent portion 125 that permits light and a line of sight for the medical staff and/or patent into the magnet bore 113.

Figure 4A:
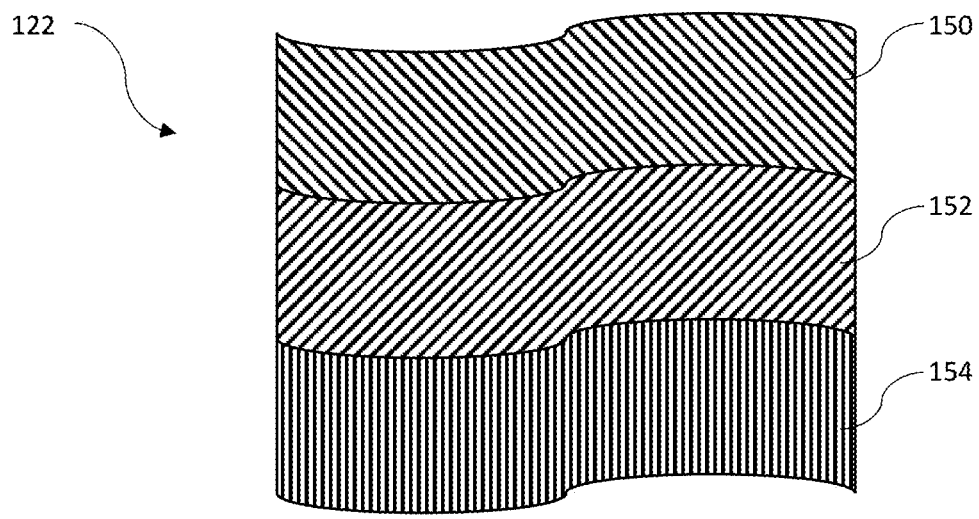
FIG. 4A illustrates the layers of a shielding cloth.

FIG. 4A illustrates a removable shielding 122. The removable shielding 122 includes multiple layers. As shown, the removable shielding 122 includes a protective layer 150, a shielding layer 152, and a thermal layer 154.

The protective layer 150 may be a fiber layer. The protective layer 150 may protect the shielding layer 152, the thermal layer 154, or both. The protective layer 150 may be located on a single side of the removable shielding 122. The protective layer 150 may sandwich the shielding layer 152, the thermal layer 154, or both. The protective layer 150 may be on a side that contacts the user. The protective layer 150 may be a soft material, a knitted material, fibrous material, a sheet of material, a non-knitted material, may be porous, transparent, include spaces that allow for some transmission of light, allow for transparency through the protective layer (e.g., visibility), or a combination thereof. The protective layer may be made of or include a natural material, a synthetic material, cotton, rayon, polyester, denim, or a combination thereof. The protective layer 150 may directly contact the shielding layer 152.

The shielding layer 152 may prevent all or a portion of the electrical field (not shown) of the portable system from passing through the removable shielding 122. The shielding layer 152 may be made of or include similar materials as the shielding discussed herein. The shielding layer 152 may include metal. The shielding layer 152 may be or include: plastic, an insulator material, an overmolding material, conductive polymers, metal grids, random metallic networks, carbon nanotubes, graphene, nanowire meshes, ultra-thin metal fins, conductive polymers, metal grids, random metallic networks, carbon nanotubes, graphene, nanowire meshes, ultra-thin metal fins, low carbon steel, no carbon steel, a steel alloy, plastic, lead, copper, graphene, brass, nickel, silver, steel, tin, or a combination thereof. The shielding layer 152 may include material that is opaque, but the shielding layer is configured to provide transparency. For example, the shielding layer 152 may include holes, a woven configuration, a mesh, or a combination thereof that allow vision through the shielding layer 152. The shielding layer 152 may prevent all or a portion of electrical field from passing through the removable shielding 122. The shielding layer 152 may be flexible. The shielding layer 152 may be connected to the protective layer 150, the thermal layer 154, or both such that the protective layer 150, the thermal layer 154, or both impart the flexibility to the shielding layer 152 or support material that once connected form the shielding layer 152. The shielding layer 152 may be a single layer of material. The shielding layer 152 may be multiple layers or pieces of shielding material that may connect together, connect to the protective layer 150, connect to the thermal layer 154, or a combination thereof.

The thermal layer 154 functions to thermally isolate an object or a user from the surrounding environment. The thermal layer 154 may retain heat so that a user of the portable system 100 may be kept warm or kept cool. The thermal layer 154 may retain heat or retain cool so that when placed over a user the thermal layer 154 provides comfort to the user. The thermal layer 154 may have a low heat conductivity value. For example, the thermal layer 154 may be insulative so that the thermal layer 154 does not provide heat or cool to the user from the surrounding area. The thermal layer 154 may provide comfort to the user. The thermal layer 154 may be or include fiberglass, mineral wool, cellulose, polyurethane foam, polystyrene, or a combination thereof. The thermal layer 154 may be connected to the shielding layer, the protective layer, or both. The removable shielding 122 may include one or more, two or more, three or more, or even four or more thermal layers 154. The thermal layer 154 may be located on a top, bottom, middle, contact a user, be opposite a side that contacts a user.

Figure 4B:
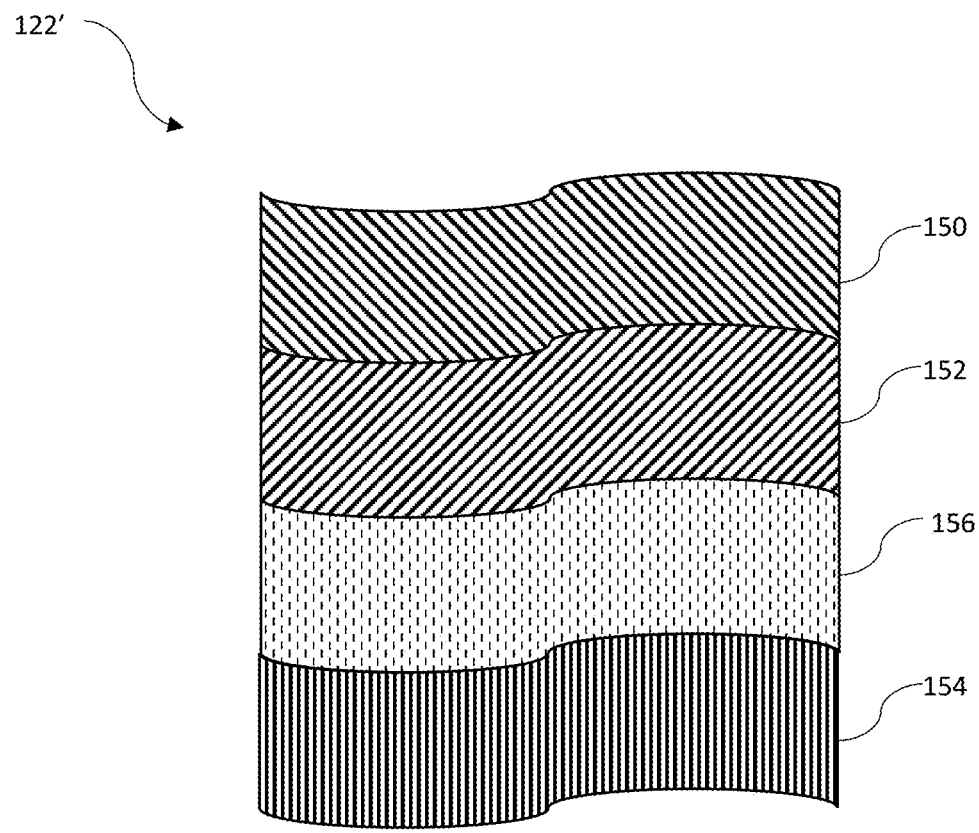
FIG. 4B illustrates layers of a shielding cloth.

FIG. 4B illustrates a removable shielding 122'. The removable shielding 122' includes multiple layers. As shown, the removable shielding 122' includes a protective layer 150, a shielding layer 152, a thermal layer 154, and a transparent layer 156. The protective layer 150, shielding layer 152, and thermal layer 154 may be the same or similar as to any of the teachings as discussed in FIG. 4A. A transparent layer 156 may be located within the removable shielding 122'.

The transparent layer 156 function to be an optically transparent material or may assist in making a removable shielding 122' transparent. The transparent layer 156 may be a film, a grid, a mesh, tubes, a network, a web, a net, or a combination thereof. The transparent layer 156 may be a layer that the shielding layer 152 may be embedded within, connected to, or both. The transparent layer 156 may include non-transparent materials but may impart strength, conductivity, support, or a combination thereof to the non-transparent materials. For example, if the non-transparent materials are a net or web the materials may be weak, but able to be seen through, and the transparent layer 156 may prevent the non-transparent materials from being damaged. The removable shielding 122' may include one or more, two or more, three or more, or even four or more transparent layers 156. The transparent layer 156 may connect or be connected to the other layers of the removable shielding 122'. The transparent layer 156 may sandwich one or more other layers (e.g., shielding layer 152).

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A portable system comprising:
   a magnet;
   a magnet bore extending through the magnet, the magnet bore configured to receive at least some portion of a patient;
   shielding that forms all or a portion of an exterior the portable system and forms a shielding area, wherein the shielding includes one or more layers, the shielding comprising:
   a material that provides magnetic shielding that reduces or prevents a static magnet field (SMF) inside of the shield area from extending outside of the shield area;
   a material that provides electromagnetic shielding and reduces or prevents a time-varying-electromagnetic field (EMF) from extending outside of the shield area or into the shield area of the portable system;
   a removable shielding that is removable or movable, wherein the patient is able to move into and out of the magnet bore when the removable shielding is in a moved position or a removed position and the removable shielding is configured to completely close the shield area so that the portable system is operative, wherein the removable shielding is flexible so that the removable shielding is conformable to the opening and the patient when all or a portion of the patient is within the magnetic bore; and
   a shielding adapter covering a connection of devices and extending from the exterior of the portable system into the magnet bore of the portable system;
   wherein the removable shielding reduces or prevents the SMF from extending outside of the shield area; the EMF from entering the magnet bore of the portable system; or both;
   wherein all or a portion of the removable shielding includes a transparent portion that is transparent; and
   wherein the portable system is self-contained and movable from place to place so that once the portable system is moved to a location of interest the portable system is plugged in and functions.

2. The portable system of claim 1, wherein the portable system is a portable magnetic resonance imaging (MRI) system, a portable magnetic resonance spectroscopy (MRS) system, or both.

3. The portable system of claim 1, wherein the shielding comprises a rear shielding that is located opposite the opening and all or a portion of the rear shielding is transparent so that light is able to penetrate the rear shielding or for visibility between the patient and medical staff.

4. The portable system of claim 1, wherein the material of the shielding that reduces or prevents the SMFs, the EMFs, or both is made of or includes a foil, a mesh, a net, or a combination thereof.

5. The portable system of claim 1, wherein the material of the shielding that reduces or prevents the SMFs is made of or includes a mumetal, low carbon steel, nickel-iron alloy, steel, or a combination thereof.

6. The portable system of claim 1, wherein the material of the shielding that reduces or prevents the EMFs is made of electrically conductive materials.

7. The portable system of claim 1, wherein the removable shielding includes the material that reduces or prevents the SMFs, the EMFs, or both.

8. The portable system of claim 1, wherein the shielding reduces a leakage of the SMF from an inside of the magnet bore to the exterior of the portable system so that the SMF is 5 Gauss or less.

9. The portable system of claim 1, wherein the shielding adapter is configured to cover a through hole that extends through the shielding so that devices may extend into the magnet bore of the portable system.

10. The portable system of claim 1, further comprising one or more movable shutting assemblies located on a first side of the magnet bore, a second side of the magnet bore, or both that entirely close the magnet bore when the portable system is not in use or is being transported; open the first end, the second end, or both so that the magnet bore is entirely open during use; or both.

11. The portable system of claim 1, wherein the shielding is configured to reduce or prevent an external EMF interference, wherein the frequency of EMF is at the range of 1 KHz to 200 MHz.

12. The portable system of claim 1, wherein the shielding comprises a front shielding that covers a front of the portable system, a rear shielding that covers a portion of a rear of the portable system, and an exterior shielding that extends between and connects the rear shielding to the front shielding.

13. The portable system of claim 12, wherein all or a portion of the front shielding, the rear shielding, or both includes the transparent portion.

14. The portable system of claim 1, wherein the shielding adapter comprises an electromagnetic filter plate that is configured to provide a sterile connection of the devices so that biomedical signals are capable of being monitored during use of the portable system.

15. The portable system of claim 14, wherein the devices comprise one or more of a temperature sensor, a blood pressure sensor, and electrocardiogram, an electroencephalograph, or an eye tracking system.

16. The portable system of claim 1, wherein the removable shielding includes a protective layer and a thermal layer.

17. The portable system of claim 1, further comprising radiofrequency coils that produce and/or receive a radio frequency and the radio frequency is from 1 MHz to 10 MHz.

18. The portable system of claim 1, further comprising radiofrequency coils that produce and/or receive a radio frequency and the radio frequency is less than 1 MHz.

19. The portably system of claim 1, wherein the shielding reduces the EMF so that the EMF passing into the shielding area is attenuated by 100 dB or more.

20. The portably system of claim 1, wherein the shielding reduces the EMF so that the EMF passing into the shielding area is attenuated by 50 dB or more.

* * * * *